US012765903B2

(12) United States Patent
Cho et al.

(10) Patent No.: US 12,765,903 B2
(45) Date of Patent: Oct. 20, 2026

(54) SHOCK WAVE LITHOTRIPSY DEVICE HAVING BREATHING TRIGGER FUNCTION

(71) Applicants: SEOUL NATIONAL UNIVERSITY HOSPITAL, Seoul (KR); HNT MEDICAL CO. LTD., Seoul (KR)

(72) Inventors: Sung Yong Cho, Seoul (KR); Jae Hak Jeong, Gyeonggi-do (KR); Sung Joung Jeon, Gyeonggi-do (KR)

(73) Assignees: SEOUL NATIONAL UNIVERSITY HOSPITAL, Seoul (KR); HNT MEDICAL CO. LTD., Seoul (KR)

( * ) Notice: Subject to any disclaimer, the term of this patent is extended or adjusted under 35 U.S.C. 154(b) by 0 days.

(21) Appl. No.: 19/117,528

(22) PCT Filed: Dec. 27, 2022

(86) PCT No.: PCT/KR2022/021372

§ 371 (c)(1),
(2) Date: Apr. 1, 2025

(87) PCT Pub. No.: WO2024/075907

PCT Pub. Date: Apr. 11, 2024

(65) Prior Publication Data

US 2026/0123948 A1 May 7, 2026

(30) Foreign Application Priority Data

Oct. 4, 2022 (KR) ........................ 10-2022-0126421
Dec. 26, 2022 (KR) ........................ 10-2022-0185003

(51) Int. Cl.
*A61B 17/00* (2006.01)
*A61B 17/225* (2006.01)

(52) U.S. Cl.
CPC .................... *A61B 17/2256* (2013.01); *A61B 2017/00017* (2013.01); *A61B 2017/00699* (2013.01)

(58) Field of Classification Search
CPC ................................................. A61B 17/2256
See application file for complete search history.

(56) References Cited

U.S. PATENT DOCUMENTS

2003/0149352 A1 8/2003 Liang et al.
2015/0342626 A1 12/2015 Hsu

FOREIGN PATENT DOCUMENTS

DE 10260594 B4 * 6/2012 ......... A61B 17/2256
JP H08-17779 B2 2/1996

(Continued)

OTHER PUBLICATIONS

International Search Report for PCT/KR2022/021372 mailed on Jun. 27, 2023.

(Continued)

*Primary Examiner* — Joseph M Santos Rodriguez
(74) *Attorney, Agent, or Firm* — PLEECHAE IP, LLC

(57) ABSTRACT

A shock wave lithotripsy device includes a shock wave generation unit that irradiates shock waves to a stone in the body of a patient, a trigger information generation unit that generates trigger information at a time point in a breathing cycle when a focus, which is set within a movement path of the stone according to breathing, matches the stone, and a control unit that controls, on the basis of the trigger information, whether or not to irradiate the shock waves from the shock wave generation unit. The shock waves can be irradiated in response to changes in the position of the stone in the body caused by breathing.

5 Claims, 5 Drawing Sheets

(56) References Cited

FOREIGN PATENT DOCUMENTS

| | | | |
|---|---|---|---|
| JP | H11-333007 | A | 12/1999 |
| JP | 2010-207427 | A | 9/2010 |
| KR | 10-2124162 | B1 | 6/2020 |

OTHER PUBLICATIONS

Office action issued on Jan. 7, 2025 from Korean Patent Office in a counterpart Korean Patent Application No. 10-2022-0185003(all the cited references are listed in this IDS.) (English translation is also submitted herewith.).

* cited by examiner

<Maximum exhalation> <Maximum inhalation>

<Sensor value not matched to trigger point>

<Sensor value matched to trigger point>

<Sensor value not matched to trigger point> <Sensor value matched to trigger point>

SHOCK WAVE LITHOTRIPSY DEVICE HAVING BREATHING TRIGGER FUNCTION

BACKGROUND

1. Technical Field

The present invention relates to a shock wave lithotripsy device incorporating a breathing trigger function.

2. Background of Invention

Extracorporeal shock wave lithotripsy is a treatment that crushes stones in a human body by focusing shock waves generated outside the human body on a site where the stones are present within the body.

The position of most stones in the body may be confirmed using an X-RAY device or an ultrasound device of a shock wave lithotriptor. When using an ultrasound device, it is possible to continuously observe the location of stones in the body, but when using the X-RAY device, continuous observation of stones is difficult due to an amount of radiation exposure.

On the other hand, even if it is possible to continuously check the location of the stone using the ultrasound device, a patient breathes continuously and the location of the stone may slightly change depending on the patient's breathing. A minimal change in the position of the stone may cause a problem in that the shock waves are not accurately radiated onto the stone.

Due to the above problem, when shock waves are irradiated onto a site where no stone exists, large or small damage may occur in body tissue.

SUMMARY

An object of the present invention is to provide a shock wave lithotripsy device incorporating a breathing trigger function that can irradiate shock waves in response to changes in the position of stones in the body of a patient caused by breathing.

1. A shock wave lithotripsy device, including: a shock wave generation unit configured to emit shock waves to stones in the body of a patient;
   - a trigger information generation unit configured to generate trigger information at a time point in a breathing cycle where a focus set within the stone's movement path according to breathing matches the stone; and
   - a control unit configured to control whether or not to emit shock waves from the shock wave generation unit based on the trigger information.
2. The shock wave lithotripsy device of the above 1, further including a breathing sensor unit configured to measure a respiratory volume over time to obtain the breathing cycle.
3. The shock wave lithotripsy device of the above 1, further including an imaging unit configured to check a degree of movement of the stone due to breathing.
4. The shock wave lithotripsy device of the above 1, wherein the trigger information generation unit sets a reference point in the breathing cycle and generates trigger information when the breathing reaches the reference point.
5. The shock wave lithotripsy device of the above 1, wherein the control unit operates the shock wave generation unit when it is determined that the trigger information matches the focus and the stone.

6. The shock wave lithotripsy device of the above 1, wherein the control unit includes: an input unit configured to generate an input signal; a storage unit configured to store the trigger information when the input signal is transmitted while the trigger information is being generated by the trigger information generation unit; and a controller unit configured to generate shock waves by driving the shock wave generation unit based on the trigger information stored in the storage unit.
7. The shock wave lithotripsy device of the above 1, wherein the control unit stops the operation of the shock wave generation unit when the breathing cycle of the patient deviates from the average breathing cycle.

The shock wave lithotripsy device of the present invention can emit and direct shock waves in response to changes in the position of stones in the body of a patient caused by breathing. According to this, shock waves may irradiate the exact location of the stone, effectively preventing shock waves from being radiated to other sites where no stone exists.

DETAILED DESCRIPTION

Figure 1:
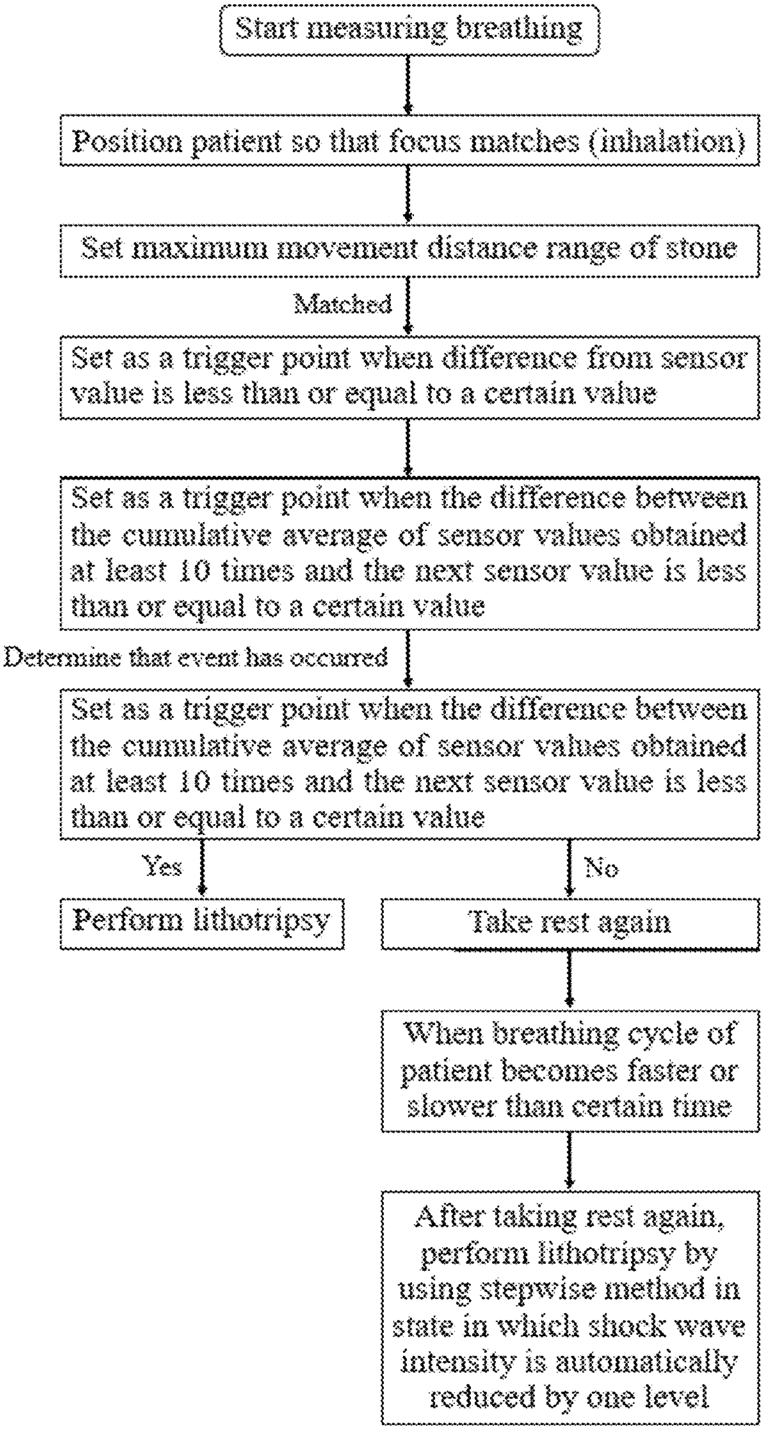
FIG. 1 is a process diagram of a stone crushing method, that is, a lithotripsy method using a shock lithotripsy device according to an embodiment of the present invention.

Hereinafter, the present invention will be described in detail.

The present invention provides a shock wave lithotripsy device.

The shock wave lithotripsy device of the present invention may include a shock wave generation unit, a trigger information generation unit and a control unit.

The shock wave generation unit emits and directs shock waves to stones in the patient's body and is electrically connected to the control unit.

The shock wave generation unit may include a bed unit on which the patient is positioned, a radiation unit that generates shock waves to target stones in the body, and a regulation unit that controls the radiation unit.

The trigger information generation unit generates trigger information.

The trigger information is information for detecting variables that vary depending on the patient's breathing so that the shock wave generation unit may generate shock waves according to the location of the stone in the patient's body, which changes depending on the patient's breathing. Using trigger information to control the timing at which shock waves are emitted from the shock wave generation unit, shock waves may be accurately delivered to the location of the stone that changes depending on the patient's breathing.

The breathing cycle is taken into account to generate trigger information. Breathing may be easily monitored, and the stone moves due to breathing so that, when breathing is stable, the breathing cycle shows regularity, which in turn results in regularity in the movement of the stone. Therefore, the shock wave lithotripsy device of the present invention may generate trigger information in consideration of the breathing cycle, thereby reducing the possibility of inaccurate irradiation of shock waves due to the movement of the stone caused by breathing.

The trigger information generation unit generates trigger information at a time point in the breathing cycle when the focus set within the movement path of stone according to breathing matches the stone.

The focus may be a focus identified in images such as ultrasound or X-ray.

The focus may be set within the movement path of the stone according to breathing. Since the stone moves due to breathing, the breathing cycle may be matched to the stone's movement path, and a location of the focus is not limited as long as the focus is within the movement path. For example, it may be set at the position where the stone exists during maximum inhalation, the position where the stone exists during maximum exhalation, or the position where the stone exists when the air inflow amount is 0.

The trigger information generation unit may set a reference point in the breathing cycle and generate trigger information when breathing reaches the reference point. The reference point is not limited as long as it is a point in the breathing cycle, and may be selected in various ways, such as at the point of maximum inhalation, at the point of maximum exhalation, or at the point when the air inflow amount is 0. Afterwards, trigger information may be generated when breathing reaches the reference point.

The shock wave lithotripsy device of the present invention may include a breathing sensor unit that measures a respiratory volume over time to obtain a breathing cycle.

The breathing sensor unit may monitor the breathing cycle. This allows the respiratory volume and breathing cycle to be obtained.

Further, the shock wave lithotripsy device of the present invention may include an imaging unit that checks a degree of stone movement due to breathing.

The imaging unit may use imaging units known in the art, such as ultrasound, X-ray or the like.

The focus of the shock wave generation unit may also be confirmed in the imaging unit. If necessary, the imaging unit may display the color of the focus to be changed when the focus matches the stone.

The control unit may control whether or not to emit shock waves from the shock wave generation unit based on trigger information, and may be electrically connected to the shock wave generation unit.

According to the control unit, the timing at which the shock wave is emitted from the shock wave generation unit is controlled using the trigger information generated by the detection unit, such that the shock wave may accurately target the location of the stone that changes according to the patient's breathing.

The control unit may cause the shock wave generation unit to operate when it is determined that the trigger information matches the focus and the stone.

In more detail, the control unit may include an input unit, a storage unit and a controller unit.

The input unit generates an input signal and is electrically connected to the storage unit. The input unit may generate the input signal when an operator presses an input button.

The storage unit stores the trigger information when the input signal is transmitted while the trigger information is being generated by the trigger information generation unit, and is electrically connected to the input unit.

For example, if the operator presses the input button at the time point where the focus matches the location of the stone in the patient's body, trigger information and breathing information at this point may be stored. For a specific example, after obtaining the patient's breathing information, the average and standard deviation of the breathing cycle are acquired and a reference point is set so that, when the next breathing reaches the reference point (e.g., in the case of the average time of one breathing cycle±standard deviation from the previous reference point), trigger information may be set.

The control unit may control the shock wave generation unit to stop operation when the patient's breathing cycle deviates from the average breathing cycle.

If the patient's breathing cycle becomes irregular and deviates from the average breathing cycle, the movement of stone also becomes irregular. Accordingly, the control unit may control the shock wave generation unit to stop operation in such cases. After stopping operation, the patient's breathing is continuously monitored, and when breathing becomes stable and reaches the average breathing cycle again, operation of the shock wave generation unit may be resumed.

Further, the present invention provides a method for crushing stones, that is, a lithotripsy method.

The lithotripsy method of the present invention generates trigger information at a time point in the breathing cycle where a focus matches the stone in a patient positioned so that the focus of the shock wave lithotripsy device is present within a movement path of the stone according to breathing, and controls whether or not to emit shock waves based on the trigger information, thereby performing lithotripsy.

According to the method of the present invention, the patient's breathing may be measured from before lithotripsy of the stone until the end of lithotripsy.

According to the method of the present invention, a stone image may be captured while setting trigger information, determining whether the focus matches the trigger information, and resetting the focus when breathing is disturbed. This process may be conducted with x-rays, ultrasound or the like.

The focus may be set within the movement path of the stone according to breathing. Since the stone moves due to breathing, the breathing cycle may be matched to the movement path of the stone, and the location of the focus is not limited as long as it is set within the movement path. For example, the focus may be set to the position where the stone exists during maximum inhalation, the position where the stone exists during maximum exhalation, or the position where the stone exists when the air inflow amount is 0.

A reference point may be set in the breathing cycle, and trigger information may be generated when the breathing reaches the reference point. The reference point is not limited as long as it is a point in the breathing cycle, and may be set in various ways, such as at the point of maximum inhalation, at the point of maximum exhalation, or at the point when the air inflow amount is 0. Thereafter, trigger information may be generated when breathing reaches the reference point.

Whether or not to emit shock waves may be controlled based on trigger information. For example, when it is determined that the trigger information matches the focus and the stone, the shock wave generation unit may operate to emit shock waves.

For example, when the operator presses the input button at the time point where the focus matches the location of the stone in the patient's body, trigger information and breathing information may be stored. For a specific example, after obtaining the patient's breathing information, the average and standard deviation of the breathing cycle are acquired and a reference point is set so that, when the next breath reaches the reference point (e.g., in the case of the average time of one breathing cycle±standard deviation from the previous reference point), trigger information may be set.

According to the method of the present invention, if the patient's breathing cycle deviates from the average breathing cycle, the operation of the shock wave generation unit may be stopped. After cessation of operation, the patient's breathing will continue to be monitored so that shock wave irradiation may be resumed when breathing becomes stable and then reaches the average breathing cycle again.

EXAMPLES

Hereinafter, the lithotripsy method using the shock wave lithotripsy device of the present invention according to an embodiment of the present invention will be described with reference to the process diagram of FIG. 1.

<Measurement Parameters: Location of Stones as Well as Kidneys During Specific Breathing (Maximum Inhalation)>

Figure 2:
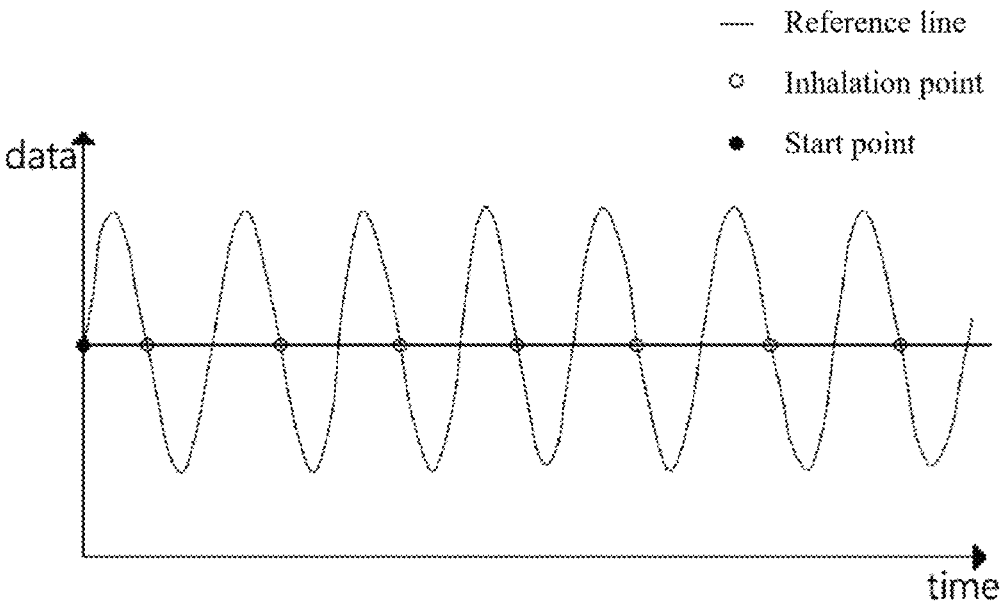
FIG. 2 is a breathing cycle graph obtained according to an embodiment of the present invention.
Figure 3:
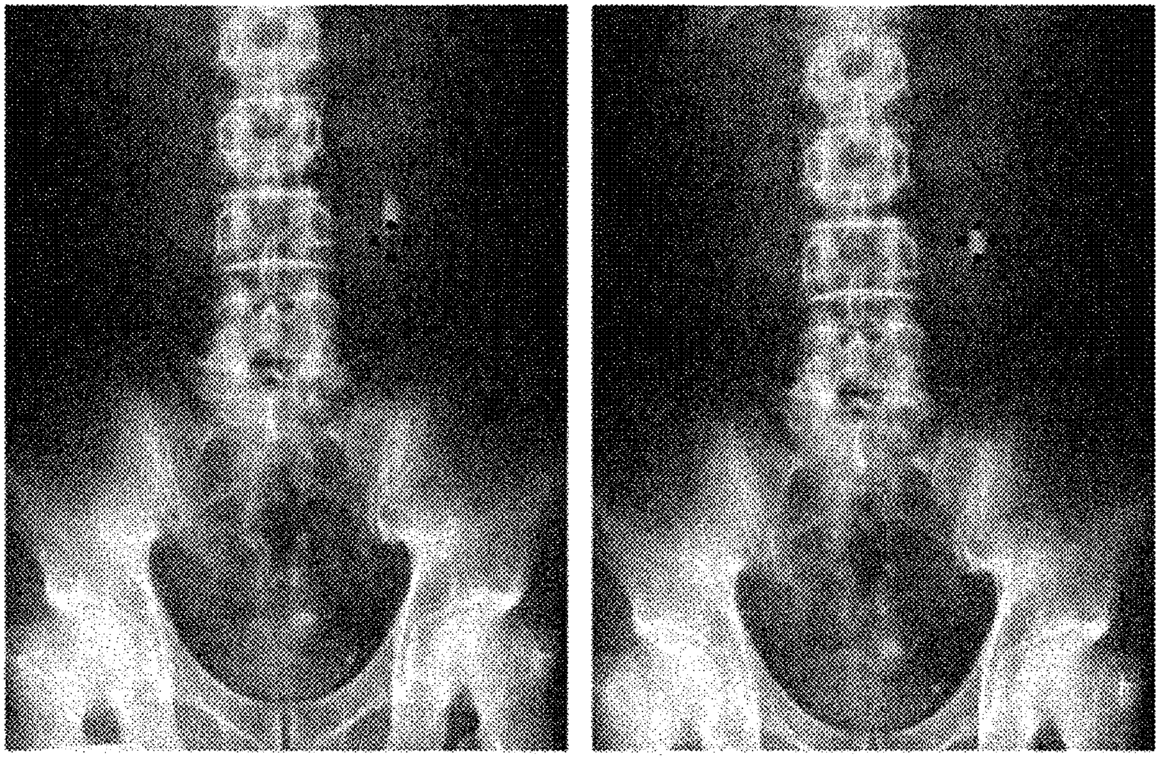
FIG. 3 is an X-ray image of the patient in maximum exhalation and inhalation states obtained according to an embodiment of the present invention.

1. Breathing of a patient is detected by the breathing sensor unit, and the time point where the air inflow amount becomes 0 is set as the reference point (FIG. 2). Y-axis of the graph is the air flow rate (L), and X-axis is time(s).
2. The patient lies on a lithotripsy bed before lithotripsy. To measure breathing in a stable state, the patient inhales and exhales loudly to stabilize breathing (up to 1 minute).
3. By determining a location of the stone at maximum inhalation/exhalation with X-ray, a range of the maximum movement distance of the stone is set.
4. In FIG. 1, an inhalation point is continuously marked with blue dots. The reason for measuring the inhalation point (read sensor value) is to determine the breathing cycle. As Y value at the inhalation point continues to be 0, X value is checked.
5. The inhalation point (read sensor value) is acquired a certain number of times (approximately 10 times) or more, and the average and standard deviation of the breathing cycle are obtained.
6. After checking the location of the stone through X-ray, the screen is held in a fixed state.
7. The ends of both sides and the top and bottom of the stone in the patient, as seen on the screen, are designated to set focus (green) on the stone (FIG. 3).
8. When breathing, the patient is positioned so that the X-ray focuses on the maximum (inhalation) of repeated movement of the stone (which is a state that stone is down). By adjusting the C-arm about 15° left and right, whether the focus is correct should be checked.
   The focus in the X-ray is the same as the inhalation point on the breathing graph.
9. It is checked whether the inhalation point on the breathing graph matches the maximum inhalation state on the X-ray.
10. If the next inhalation point (reference point) has a difference within the average±standard deviation of the previous reference point with respect to the average value (average value of the breathing cycle) of the inhalation point (read sensor value), trigger information is set by entering the set button.
11. Using the measured breathing cycle, if the patient's breathing cycle on average becomes faster or slower than a predetermined time, it is determined that an event has occurred, and lithotripsy proceeds with the shock wave intensity automatically reduced by one level.
12. Once the stone is in focus, the sensor value is read by clicking on the image during breathing (time point in the breathing cycle).
13. Under X-ray or ultrasound observation, if the stone moves within a predetermined distance (mm), lithotripsy progresses. Otherwise, the patient takes rest again to stabilize their breathing.
14. Gel is applied to a generator (the part where the shock wave is emitted) of lithotripsy device to ensure that ultrasonic measurements and shock waves are transmitted well.
15. After informing the patient of the start of lithotripsy, the process begins by giving a mild shock (while monitoring breathing measurements until lithotripsy is complete).
16. One minute after starting lithotripsy, the breathing cycle is measured to evaluate breathing regularity.
   If breathing is unstable, the lithotripsy device automatically stops shock wave emission. After resting for one minute, the lithotripsy device delivers shock waves again.
   If breathing is stable, the device proceeds with lithotripsy.
17. When a shock occurs, the intensity is gradually increased step-wise every 500 times (the number of times may be changed).
   When the patient feels pain, the intensity is adjusted to the preceding level.
   The total number of shocks may be up to 3,000 (At this time, if the accuracy rate is high, stone fragmentation may be achieved in fewer shocks, allowing for earlier completion of the procedure.)
18. X-ray confirmation is performed through C-arm for every 500 shocks.
   When the stone is pulverized, lithotripsy is halted (The image is evaluated every 500 shocks, and the procedure is terminated upon confirmation of stone fragmentation)
19. If, due to actions of the patient, such as speaking or moving in pain, the focus of the stone fixed by ultrasonic waves deviates and breathing becomes disturbed (if it differs from the average breathing cycle), the lithotripsy device would temporarily stop the shock wave, and the lithotripsy technician will move the patient or the lithotripsy bed to adjust the focus of the ultrasonic wave to the stone again.
20. If breathing becomes regular again based on the breathing measurement, the lithotripsy device resumes operation after one minute of pause, and the shock wave is emitted again.
21. At this time, if the patient takes a deep breath, the shock wave reassesses the location of the stone again when the kidney moves down to the bottom, and then starts lithotripsy.
22. It is set to ignore data if the trigger point recurs continuously within the specified delay time. In other words, if it is confirmed that the breathing cycle continuously satisfies the range of the mean±standard deviation, it is determined that the breathing cycle has recovered, and lithotripsy is resumed.

23. It is checked whether stones, the focus and trigger points are well matched, every few minutes during the procedure. If such checking is continuously done using X-rays, it may cause excessive exposure to radiation. Therefore, breathing and ultrasound are used for checking.

Figure 4:
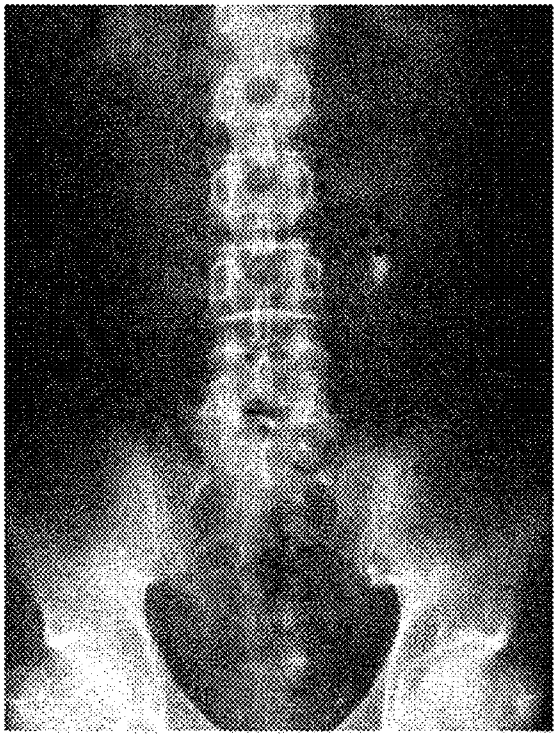
FIGS. 4 and 5 show the focus when the focus (trigger point) and the breathing cycle (the movement path of the stone according to the breathing cycle) match and do not match in the X-ray images and ultrasound images, respectively.
Figure 4:
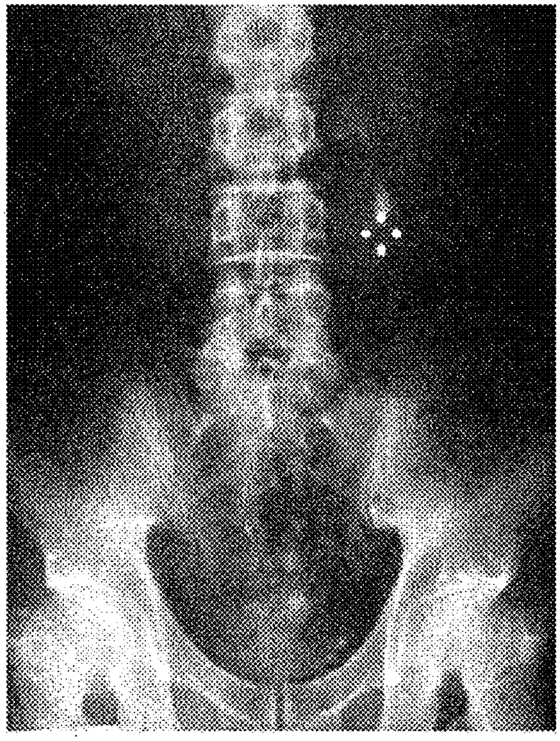
Figure 5:
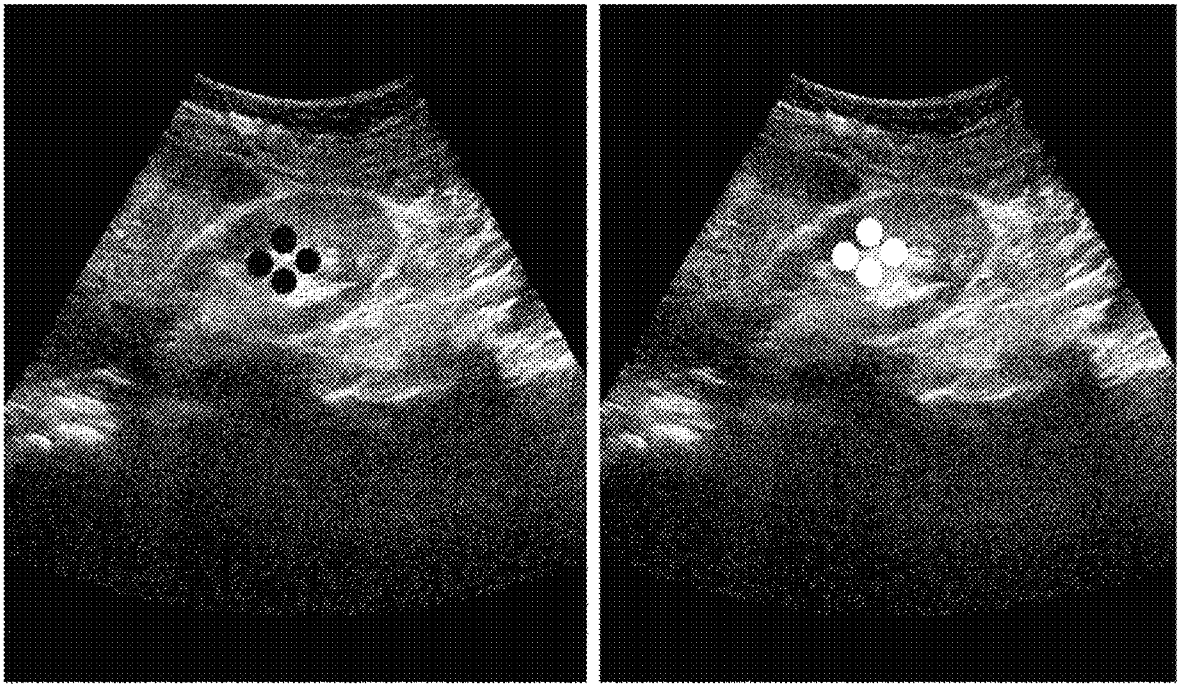

24. After setting the trigger point, the focus color changes (green→red) when the sensor value (inhalation point in the graph: 0) matches the trigger point, thereby confirming the degree of focus deviation (FIGS. 4 and 5).

25. If the stone is not present when the focus color changes, the bed is moved to correct the location of the stone (using X-ray or ultrasound).

What is claimed is:

1. A shock wave lithotripsy device comprising:

a shock wave generation unit configured to emit shock waves toward a stones inside the body of a patient;

a breathing sensor unit configured to measure a respiratory volume over time to obtain a breathing cycle;

an imaging unit configured to capture a stone image by imaging the stone in the body, and identify a movement path and a maximum movement distance of the stone due to breathing based on the stone image;

a storage configured to store trigger information, wherein the trigger information controls the timing at which the shock waves are emitted from the shock wave generation unit, and is set based on continuous tracking of a movement of the stone in accordance with the breathing to a time point in the breathing cycle where a focus set within the movement path of the stone matches the stone moving in accordance with the breathing; and a processor electrically connected to the shock wave generation unit, and configured to control whether or not to emit the shock waves from the shock wave generation unit based on the trigger information.

2. The shock wave lithotripsy device according to claim 1, further comprising: a trigger information generation unit configured to set a reference point in the breathing cycle and generate the trigger information when the breathing reaches the reference point.

3. The shock wave lithotripsy device according to claim 1, wherein the processor operates the shock wave generation unit when it is determined that the breathing cycle of the patient reaches a time point corresponding to the trigger information where the focus matches the stone.

4. The shock wave lithotripsy device according to claim 3, further comprising:

an input unit configured to generate an input signal;

wherein the storage is configured to store the trigger information when the input signal is received while the trigger information is being generated by the trigger information generation unit; and wherein the processor is configured to cause the shock wave generation unit to emit the shock waves based on the trigger information stored in the storage.

5. The shock wave lithotripsy device according to claim 1, wherein the processor stops the operation of the shock wave generation unit when the breathing cycle of the patient deviates from a predetermined average breathing cycle.

* * * * *